United States Patent
Bourang et al.

(10) Patent No.: US 12,274,633 B2
(45) Date of Patent: Apr. 15, 2025

(54) STENT RETENTION

(71) Applicant: Advanced Bifurcation Systems Inc., Livermore, CA (US)

(72) Inventors: Ashur Bourang, Turlock, CA (US); Henry Bourang, Turlock, CA (US)

(73) Assignee: Advanced Bifurcation Systems Inc., Livermore, CA (US)

( * ) Notice: Subject to any disclaimer, the term of this patent is extended or adjusted under 35 U.S.C. 154(b) by 228 days.

(21) Appl. No.: 17/885,723

(22) Filed: Aug. 11, 2022

(65) Prior Publication Data

US 2023/0042061 A1 Feb. 9, 2023

Related U.S. Application Data

(62) Division of application No. 17/198,685, filed on Mar. 11, 2021, now Pat. No. 11,452,629.

(60) Provisional application No. 62/988,132, filed on Mar. 11, 2020.

(51) Int. Cl.
*A61F 2/95* (2013.01)
*A61F 2/958* (2013.01)

(52) U.S. Cl.
CPC ............ *A61F 2/9525* (2020.05); *A61F 2/958* (2013.01); *A61F 2002/9583* (2013.01); *A61F 2210/0019* (2013.01); *A61F 2250/0098* (2013.01)

(58) Field of Classification Search
CPC ........ A61M 25/10187; A61M 25/0074; A61M 25/10181; A61M 2025/0166; A61M 2205/18; A61B 17/221; A61B 2017/00336; A61B 2017/00358; A61F 2/9525; A61F 2/958; A61F 2210/0019; A61F 2250/0098; A61F 2/9524; A61F 2/9522

See application file for complete search history.

(56) References Cited

U.S. PATENT DOCUMENTS

| | | | |
|---|---|---|---|
| 7,351,255 B2 | 4/2008 | Andreas | |
| 7,563,400 B2 | 7/2009 | Wilson et al. | |
| 7,947,207 B2 | 5/2011 | Mcniven et al. | |
| 8,318,078 B2 | 11/2012 | Jagger et al. | |
| 10,137,015 B2 | 11/2018 | Holzer et al. | |
| 11,452,629 B2 | 9/2022 | Bourang et al. | |

(Continued)

FOREIGN PATENT DOCUMENTS

| | | |
|---|---|---|
| CN | 115279308 A | 11/2022 |
| JP | 2013523215 A | 6/2013 |

(Continued)

OTHER PUBLICATIONS

"U.S. Appl. No. 17/198,685,312 Amendment filed Aug. 11, 2022", 5 pgs.

(Continued)

*Primary Examiner* — Thomas McEvoy
(74) *Attorney, Agent, or Firm* — Schwegman Lundberg & Woessner, P.A.

(57) ABSTRACT

A system and method for a stent delivery system, the delivery system having a catheter and a balloon coupled to a distal portion of the catheter. The catheter with the radially expandable member is inserted into a cavity in a mold. Heat and pressure are applied for a period of time which inflates the balloon and imparts a shape memory to a portion of the balloon. The balloon is removed from the cavity of the mold with a shape memory.

8 Claims, 11 Drawing Sheets

(56) References Cited

U.S. PATENT DOCUMENTS

| | | |
|---|---|---|
| 2003/0208254 A1 | 11/2003 | Shortt |
| 2012/0283814 A1* | 11/2012 | Huang .................. A61F 2/958 29/515 |
| 2012/0290063 A1 | 11/2012 | Wang et al. |
| 2014/0100647 A1 | 4/2014 | Bourang |
| 2016/0096308 A1 | 4/2016 | Bar et al. |
| 2021/0282951 A1 | 9/2021 | Bourang et al. |

FOREIGN PATENT DOCUMENTS

| | | |
|---|---|---|
| JP | 2023517028 A | 4/2023 |
| WO | WO-2011119879 A1 | 9/2011 |
| WO | WO-2021183746 A1 | 9/2021 |

OTHER PUBLICATIONS

"U.S. Appl. No. 17/198,685, Non Final Office Action mailed Jan. 21, 2022", 7 pgs.
"U.S. Appl. No. 17/198,685, Notice of Allowance mailed May 12, 2022", 7 pgs.
"U.S. Appl. No. 17/198,685, PTO Response to Rule 312 Communication mailed Aug. 18, 2022", 2 pgs.
"U.S. Appl. No. 17/198,685, Response filed Apr. 5, 2022 to Non Final Office Action mailed Jan. 21, 2022", 6 pgs.
"U.S. Appl. No. 17/198,685, Response filed Nov. 29, 2021 to Restriction Requirement mailed Oct. 1, 2021", 8 pgs.
"U.S. Appl. No. 17/198,685, Restriction Requirement mailed Oct. 1, 2021", 6 pgs.
"International Application Serial No. PCT/US2021/021875, International Search Report mailed May 25, 2021", 2 pgs.
"International Application Serial No. PCT/US2021/021875, Written Opinion mailed May 25, 2021", 5 pgs.
U.S. Appl. No. 17/198,685, U.S. Pat. No. 11,452,629, filed Mar. 11, 2021, Stent Retention.
"European Application Serial No. 21766825.0, Extended European Search Report mailed Feb. 20, 2024", 8 pgs.
"European Application Serial No. 21766825.0, Response to Communication pursuant to Rules 161(2) and 162 EPC filed Apr. 20, 2023", 12 pgs.
"European Application Serial No. 21766825.0, Response filed Sep. 11, 2024 to Extended European Search Report mailed Feb. 20, 2024", 13 pgs.
"Japanese Application Serial No. 2022-553078, Notification of Reasons for Refusal mailed Dec. 13, 2024", w/ English Translation, 9 pgs.
"Japanese Application Serial No. 2022-553078, Response filed Feb. 26, 2025 to Notification of Reasons for Refusal mailed Dec. 13, 2024", W/English Claims, 18 pgs.

* cited by examiner

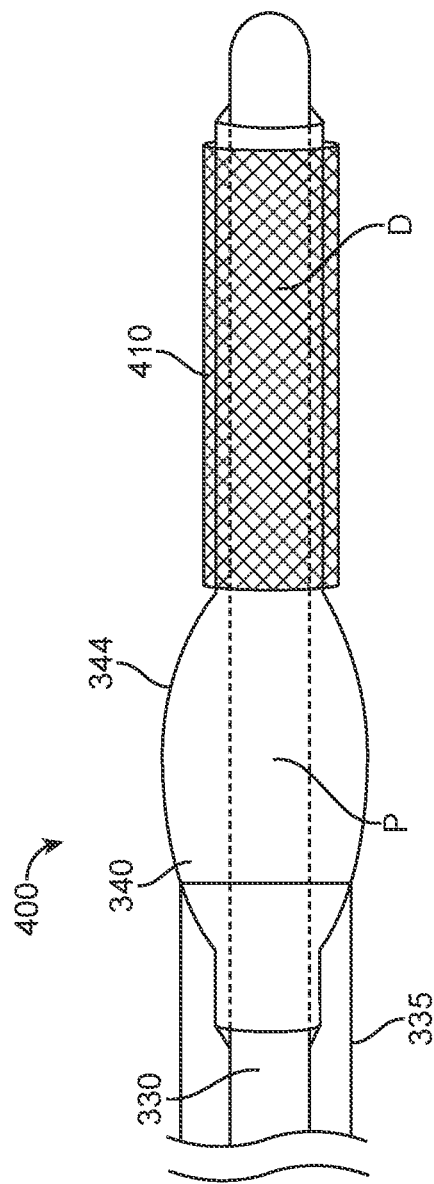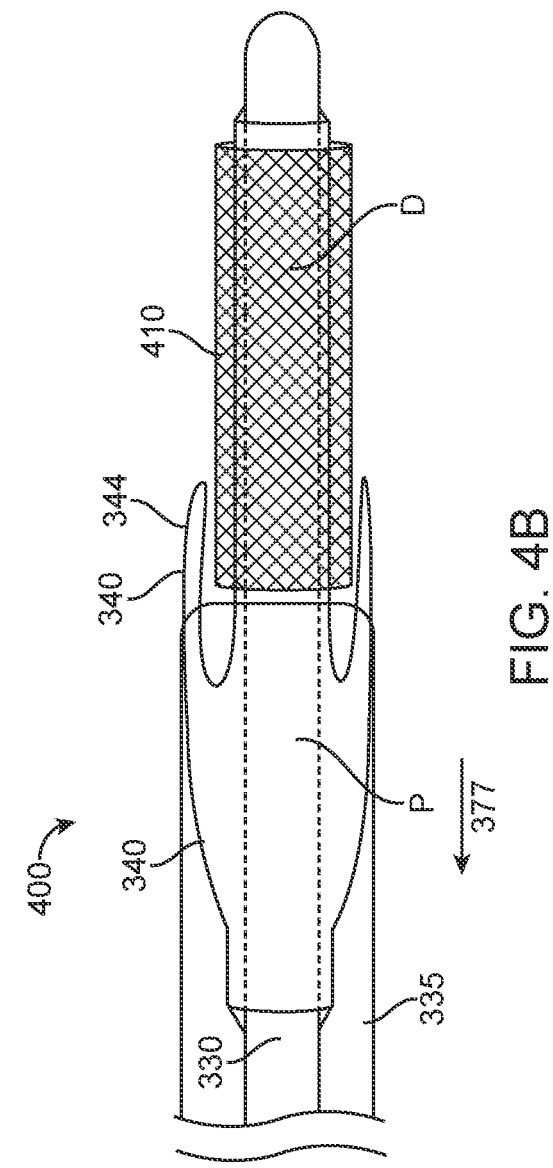
FIG. 4A
FIG. 4B

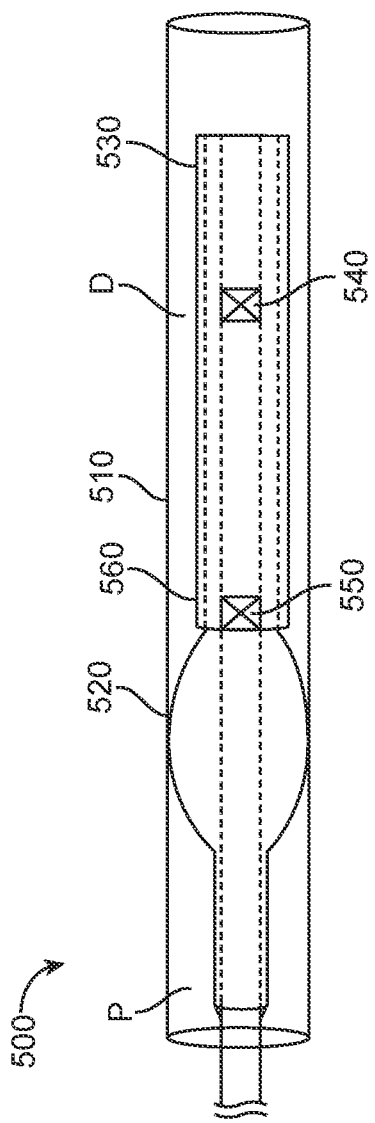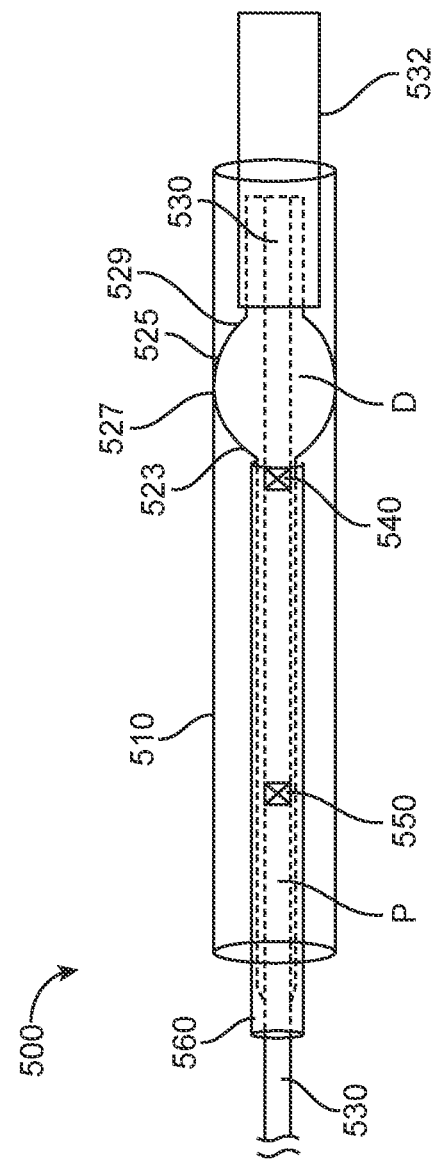

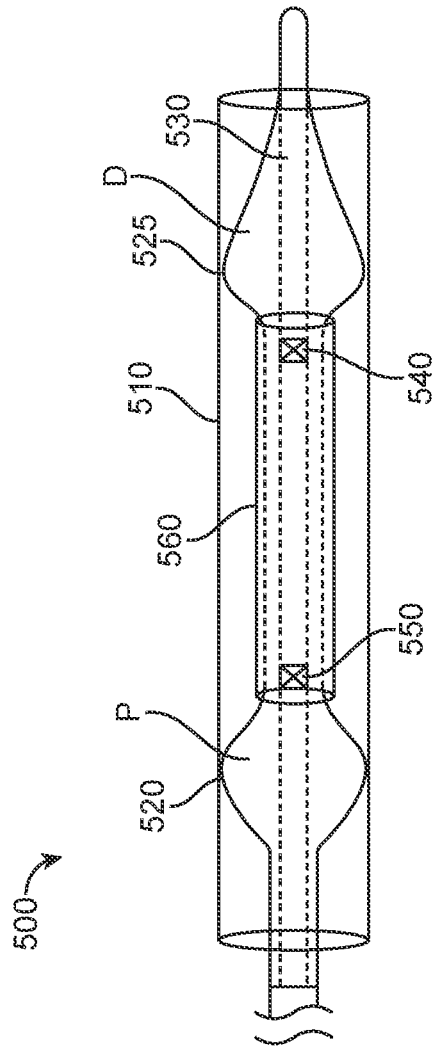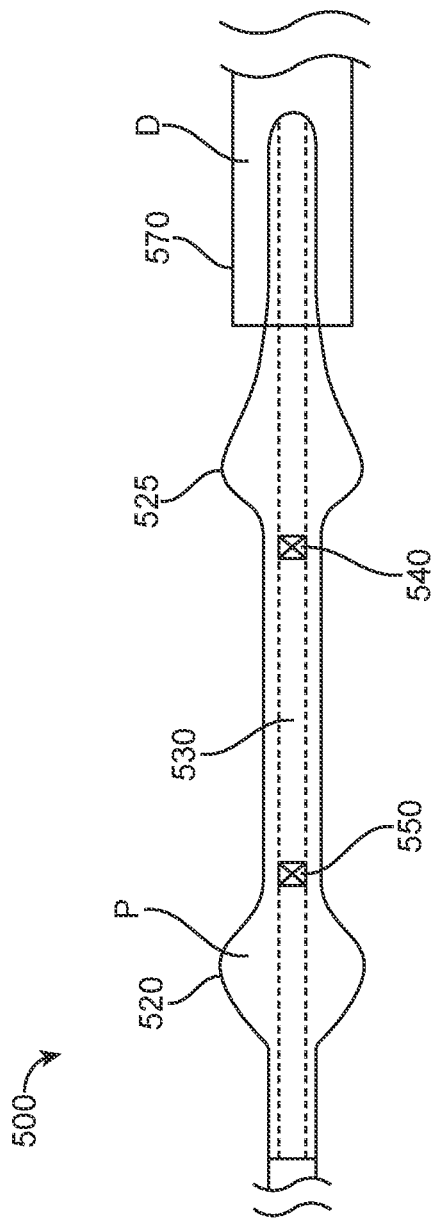
FIG. 5C
FIG. 5D

STENT RETENTION

RELATED U.S. APPLICATION DATA

The present application is a divisional of U.S. patent application Ser. No. 17/198,685, filed on Mar. 11, 2021, now U.S. Pat. No. 11,452,629, which is a non-provisional of and claims the benefit of U.S. Provisional Pat. No. 62/988,135, filed on Mar. 11, 2020; the entire contents of which are incorporated herein by reference.

BACKGROUND

The present invention relates to medical devices, and more particularly to stenting and treatment of bifurcated vessels. A stent is an implantable scaffold that is typically delivered percutaneously and deployed in a vein, artery, or other tubular body organ for treating an occlusion, stenosis, aneurysm, collapse, dissection, or weakened, diseased, or abnormally dilated vessel or vessel wall. The stent is radially expanded in situ, thereby expanding and/or supporting the vessel wall or body organ wall. In particular, stents are quite commonly implanted in the coronary, cardiac, pulmonary, neurovascular, peripheral vascular, renal, gastrointestinal and reproductive systems, and have been successfully implanted in the urinary tract, the bile duct, the esophagus, the tracheo-bronchial tree and the brain, to reinforce these body organs.

Stents are commonly used to restore patency to a blood vessel thereby allowing blood to flow through a blocked blood vessel. Stents are used to treat stenotic lesions in blood vessels such as coronary arteries that supply oxygen-rich blood to the heart or other parts of the body. Additionally, stents may reduce symptoms such an angina and help to treat myocardial infarctions. Stents are commonly inserted percutaneously by a catheter through an artery such as the femoral artery, radial artery, or brachial artery, and upon reaching the site of deployment, the stent is expanded, re-opening the vessel lumen and supporting the vessel walls, and the catheter is removed leaving the stent in place.

Conventional stent technology is relatively well developed. Conventional stent designs typically feature a straight tubular, single type cellular structure, configuration, or pattern that is repetitive through translation along the longitudinal axis. In many stent designs, the repeating structure, configuration, or patterns has strut and connecting balloon catheter portions that can impede blood flow at vessels. Further, the configuration of the struts and connecting balloon catheter portions may obstruct the use of post-operative devices to treat vessels.

Therefore, given the challenges of current stent manufacture and stent technology used for treating vascular conditions, a need exists for improved stent delivery systems, methods of delivery and fabrication. At least some of these objectives will be met by the present invention.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in figures of the accompanying drawings.

FIG. 4A illustrates a side view of a stent loaded onto a radially expandable member after processing in the mold.

FIG. 4B illustrates a side view of a pillow protecting the stent from engaging an edge of the sheath.

FIG. 5A illustrates a side view of a pillow on the proximal end of the radially expandable member.

FIG. 5B illustrates a side view of a pillow on the distal end of the radially expandable member.

FIG. 5C illustrates a side view of pillows on the proximal and distal ends of the radially expandable member.

FIG. 5D illustrates another view of FIG. 5C after being removed from the mold.

DETAILED DESCRIPTION OF THE INVENTION

Figure 1:
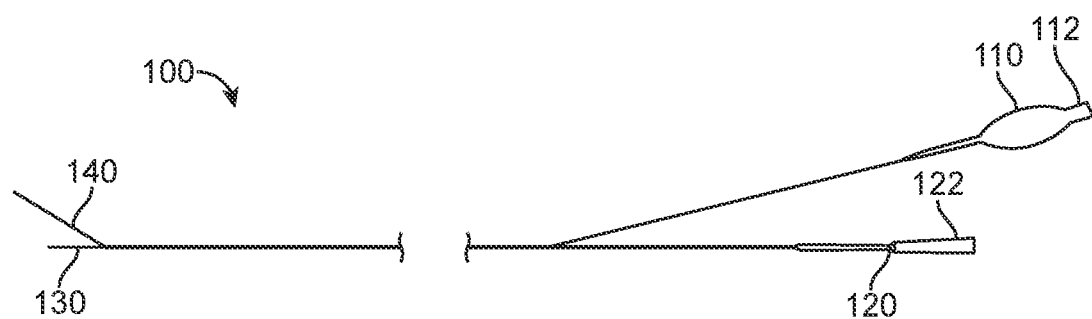
FIG. 1 illustrates a side view of a delivery system having a mother catheter and a daughter catheter.

The present invention generally relates to improving stent delivery systems, delivery methods and manufacturing techniques to make vascular treatments more precise and less likely to cause complications. For example, these systems and methods may be advantageous for mitigating the risk of damaging surrounding tissue during distal advancement through the vessel. However, this is not intended to be limiting, and one skill in the art will appreciate that the devices and methods described herein may be used for treating other regions of the body.

Aspects of the subject technology address some of the potential problems of conventional stent delivery systems, which may have limitations and challenges in stent retention while retracting the stent loaded catheter back into an introducer sheath or a guide catheter, as well as during delivery of the stent delivery system through a vessel. For example, a potential challenge of conventional stent delivery systems may occur when the proximal edge of the stent catches on the distal edge of the introducer sheath or guide catheter as the stent is being retracted proximally, causing the stent to become dislodged and/or damaged. Further, upon introduction of the catheter through a vessel, the distal edge of the stent may come into contact with tissue during distal advancement, or a proximal edge of the sent may come into contact with tissue during proximal retraction, thereby causing vessel damage or plaque snow plowing. Tissue damage may occur around curves of a tortuous vessel. Examples of stent delivery systems disclosed herein may mitigate the risk of the stent becoming caught on the introducer sheath or guide catheter or causing tissue damage while being introduced or otherwise manipulated. These challenges may be mitigated with a stent delivery system that has a "pillowed" region on either side of the stent. The pillowed region is an enlarged protrusion (e.g., bump) that may be a dumbbell shape and may protect an edge on either side of the stent from becoming dislodged from the catheter or damaging surrounding tissue upon insertion and retraction.

The proximal edge or distal edge of the stent may be shielded from dislodgement and tissue damage by use of a radially expandable member. In any examples discussed herein, the radially expandable member may be a balloon. The balloon member may have a bump on either end of the stent that may have a shape memory. The shape memory is induced by heat and pressure over time and the shape may be retained after several cycles on inflation and deflation. Additionally, the balloon may be deflated but still maintains a protective shield (e.g., a protrusion) due to a shape memory that provides protection from the proximal edge or the distal edge of the stent from coming into contact with the sheath or from coming into contact with the tissue. Thus, the balloon or other radially expandable member may be deflated and re-inflated while still providing the pillowing. The memory may last one or more, two or more, three or more, four or more, five or more, six or more, seven or more, eight or more, nine or more, or greater than ten inflation/deflation cycles before the memory is lost. The radially expandable member in this or any example may be a balloon, or another expandable member used in the deployment of the stent.

In general, the methods disclosed herein may provide protection to the stent by inducing shape memory into the balloon. For example, inducing shape memory may be accomplished by use of inserting the balloon into a mold. The mold may be made from metal, polymer, or ceramic, combinations thereof, or any other material known in the art. In any example, all or a portion of the balloon is disposed in the mold, and a portion of the balloon may be expanded in the mold while another portion is constrained inside or outside of the mold. The mold may be a hand crimper, an iris, or an elongate shaft (e.g., made out of metal, polymer, ceramic). The balloon may be processed during expansion (e.g. heat, pressure), which induces shape memory into the balloon. Throughout the application, reference D represents "distal" and P represents "proximal."

Reference will now be made in detail to specific examples of the present disclosure. In the following description, specific details are set forth in order to provide a thorough understanding of the subject matter. It shall be appreciated that any example may be practiced without some or all of these specific details and no specific feature is critical or limiting.

Stent Retention

FIG. 1 shows a side view of a stent delivery system 100 for retaining a stent, according to any example. The system comprises a first catheter 120 (e.g., mother catheter or also referred to as a main branch) with a first elongate shaft and a hub 122, and a second catheter 110 (e.g., daughter catheter also referred to as a side branch catheter) with a second elongate shaft and a hub 112. The term "mother" may refer to the catheter, balloon, or the stent in the main branch, while the term "daughter" may refer to the catheter, balloon, or the stent in the side branch. Therefore, the term 'mother' may be interchanged with the term 'main branch,' and the term 'daughter' may be interchanged with the term 'side branch.' The first catheter 120 has a first balloon 130 (e.g., mother balloon) disposed on a distal portion of the first catheter 120, and the second catheter 110 has a second balloon 140 (e.g., daughter balloon) disposed on a distal portion of the second catheter 110. A stent (not illustrated) may be disposed over the mother balloon, the daughter balloon, or stents maybe disposed over both balloons.

Figure 2A:
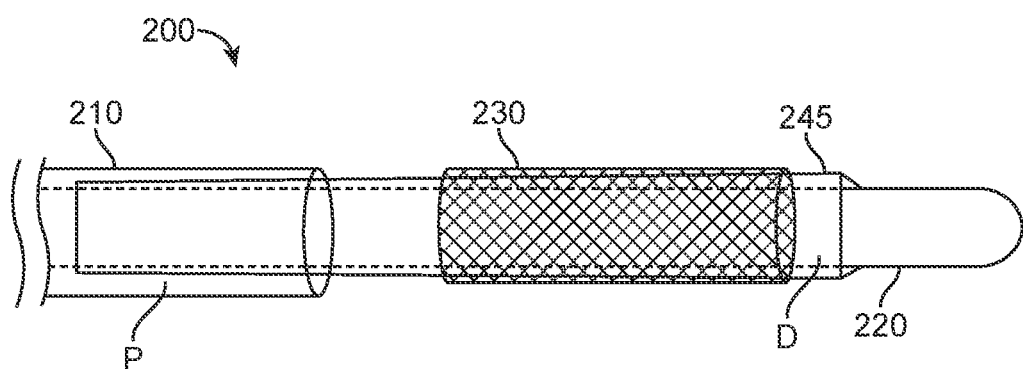
FIG. 2A illustrates a stent delivery system in a guide catheter or introducer sheath.

FIG. 2A shows a sideview of a stent delivery system 200 for retaining a stent 230, indicating the proximal side P and the distal side D of the stent delivery system 200. The system for a stent comprises a delivery catheter 220, a balloon 245 on a distal portion of a catheter 220, and a stent 230 disposed over the balloon. The balloon 245 has a working length that may match, be longer, or shorter than the stent 230 length. The balloon 245 may comprise a proximal and distal shouldered region that is connected to the catheter 220, and the catheter is slidably disposed through the guide catheter 210 (e.g., sheath). An introducer sheath or guide catheter 210 is provided in which the catheter 220 and stent 230 may be retracted proximally therethrough so that the stent is protected by the guide catheter 210 during delivery.

Figure 2B:
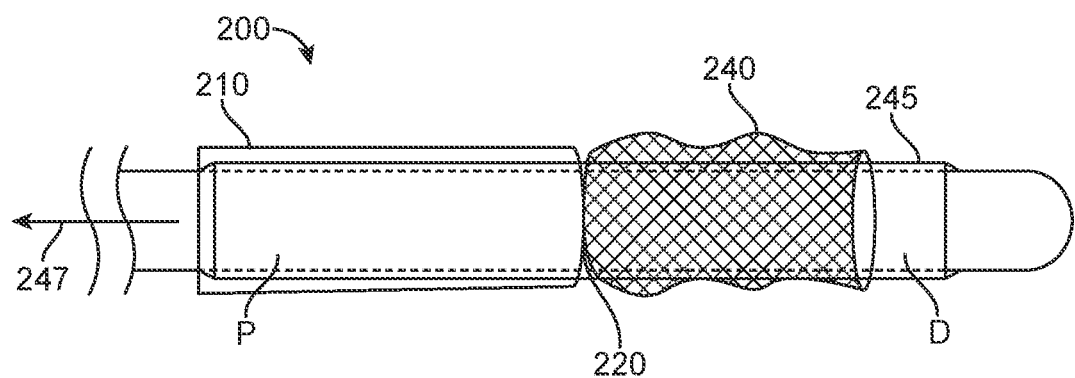
FIG. 2B illustrates a stent edge catching on an edge of the introducer sheath or guide catheter of FIG. 2A.

FIG. 2B shows a side view of the catheter 220, the balloon 245 and the stent 240 in FIG. 2A being retracted proximally as indicated by arrow 247 through the sheath or guide catheter 210. The blunt proximal edge of the stent 240 may come in contact with the distal edge of sheath or guide catheter 210 and induce compressive forces onto the stent 240. The stent may become deformed, and/or dislodged partially or entirely from the catheter. Additionally, the stent may incur damage that renders it unusable. This can be particularly undesirable when the stent carries a therapeutic agent such as paclitaxel or rapamycin or any other drug, since the drug may also be stripped off the stent when the stent catches on the sheath edge.

Figure 2C:
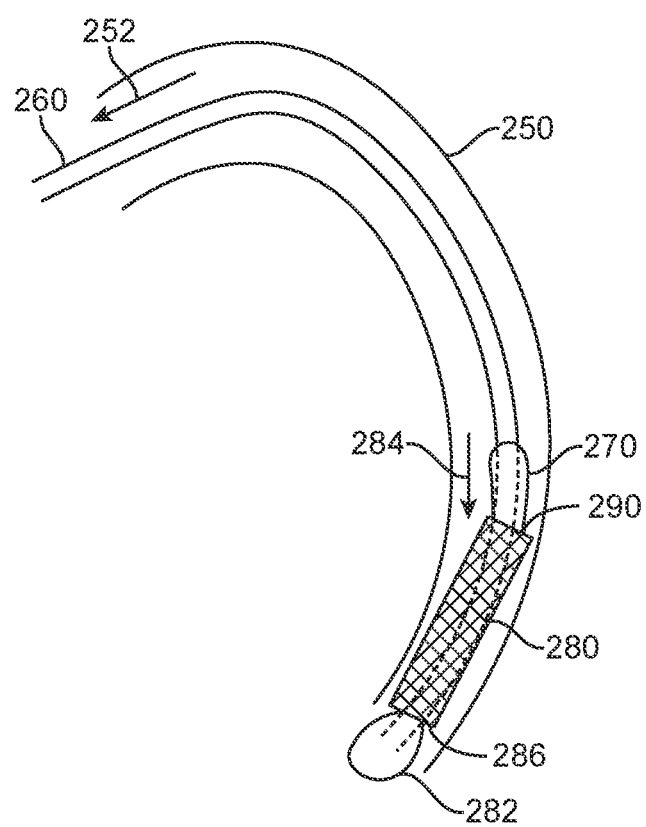
FIG. 2C illustrates a stent edge coming into contact with tissue upon delivery in a vessel.

FIG. 2C shows a side view of the catheter 260, the proximal portion 270 of the balloon and the distal portion 282 of the balloon, and the stent 280 being delivered through a vessel 250. In some examples, the vessel 250 may have an arcuate region and the blunt proximal end 290 of the stent 280 may come into contact with the wall of the vessel 250 as the catheter is retracted proximally through the vasculature as shown by arrow 252. The region of contact of the blunt proximal end 290 may cause tissue damage. Damage to the tissue may also occur during distal advancement through the vasculature as shown by arrow 284 in which the distal end 286 of the stent 280 comes into contact with the vessel 250.

Several examples of protecting one or more edges of the stent and forming a protective barrier are disclosed herein.

Shape Memory Formation:

FIGS. 3A-3D show an example of a process of forming the proximal portion of the balloon.

Figure 3A:
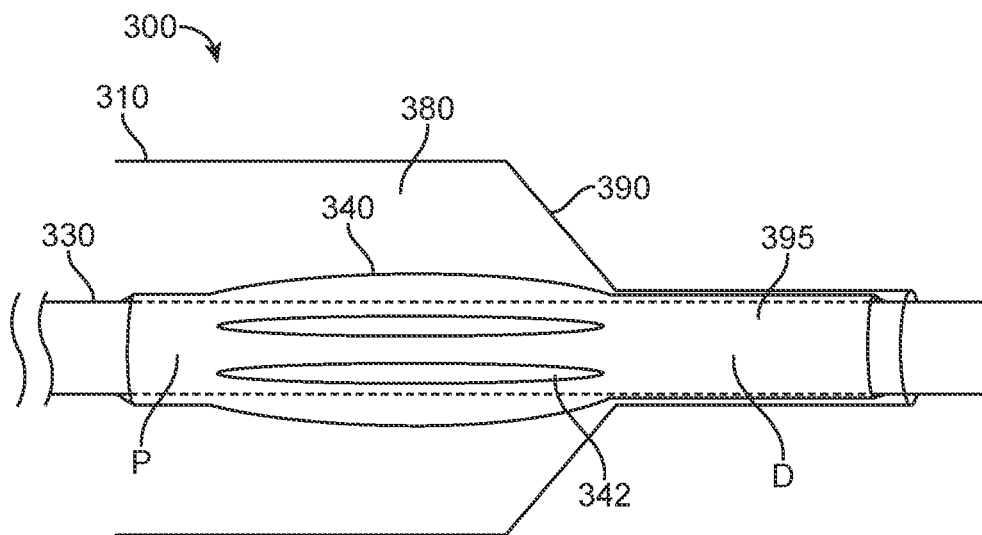
FIG. 3A illustrates a side view of a radially expandable member disposed in a mold.

FIG. 3A shows a side view of a system 300 for forming the balloon to help protect and retain a stent on a stent delivery catheter. The stent delivery system comprises a stent delivery catheter having a first catheter 330, and a folded balloon 340 on the first catheter 330. The balloon 340 may have pleats or folds 342 when the balloon 340 is in a neutral (e.g., unexpanded) state. The balloon is fixedly attached to the first catheter 330. The first catheter 330 and balloon 340 are inserted into a mold 310. The mold 310 may be made from ceramic (e.g. glass), polymer, or metal, or combinations thereof, or any other material known in the art. In this or any example, a portion of the balloon 340 may be constrained by the mold 310. The mold 310 comprises a first cavity 380, a second cavity 395, and a transition region such as a taper portion 390 may be disposed therebetween. The first cavity of the mold 310 is cylindrical and the second cavity of the mold 310 is also cylindrical, in which the first cavity 380 has a larger diameter than the second cavity 395. The mold 310 may have the same length as the balloon 340, or a larger length than the balloon 340. A proximal portion of the balloon 340 may be disposed in the first cavity 380, and a distal portion of the balloon 340 may be disposed in the second cavity 395. Additionally, a portion between the proximal portion of the balloon 340 and a distal portion of the balloon 340 may be disposed in the taper portion 390. The distal portion of the balloon 340 is disposed in the second cavity of the mold 310 and is constrained by the mold and does not allow expansion of the balloon 340 (or substantially no expansion). The first cavity 380 has a diameter that is greater than the folded balloon 340 in its unexpanded state. The first cavity 380 may have a larger diameter than the fully expanded balloon 340, which may allow the balloon 340 to fully expand. Alternatively, the first cavity 380 may have a smaller diameter than the balloon 340 in its fully expanded state, which prevents the balloon 340 from further expansion (e.g., full expansion of the balloon) after the balloon 340 abuts the inside wall of the first cavity 380. The proximal portion of the balloon 340 may expand to create a pillow region. The pillow region creates a protective cover for the edge of the stent during introduction and retraction into and out of the vasculature. The first cavity 380 is greater than or equal to the length of the pillow region on the proximal portion of the balloon 340. The second cavity 395 has a diameter sized to receive the distal portion of the balloon 340, however it constrains the distal portion of the radially expandable portion and does not allow for expansion when the balloon is heated and pressurized. The second cavity 395 is greater than or equal to the length of the distal portion of the balloon 340.

Figure 3B:
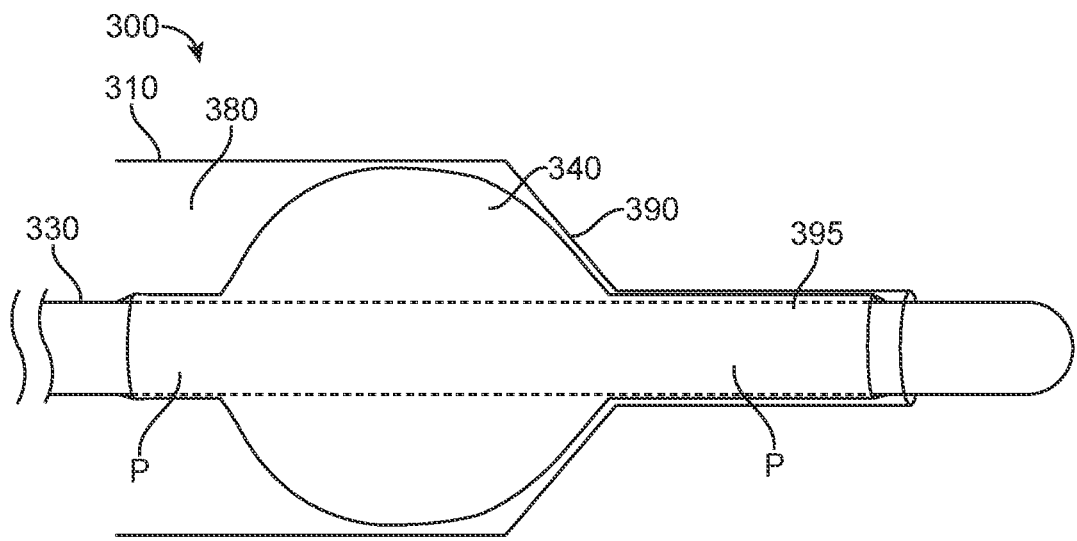
FIG. 3B illustrates a side view of radial expansion of a radially expandable member in the mold of FIG. 3A.

FIG. 3B shows a side view of a stent delivery system 300 when the balloon is pressurized shown in FIG. 3A. The balloon 340 may be expanded in the mold 310. The expansion of the balloon 340 occurs when heat is applied to the mold 310 and pressure is applied to inflate the balloon 340. The heat, pressure, and dwell time in the mold will be explained below. In one example, a proximal portion of the balloon 340 is expanded in the mold 310, while the distal portion of the balloon 340 is constrained as explained above.

The entire balloon 340 may experience heat and pressure in the mold 310, however only the proximal portion of the balloon 340 may expand as the distal portion of the balloon 340 may be constrained, and therefore unable to inflate. Additionally, an optional protective sheath 335 as shown in FIG. 4A below, may be applied to a portion of the balloon 340 in the mold to prevent inflation. The constrained portion of the balloon 340 has a smaller diameter than the unconstrained portion of the balloon 340 as shown in FIG. 4A.

In any example, a proximal portion of the balloon 340 may be inflated to contact the inside walls of the first cavity 380, and a distal portion of the balloon 340 is constrained and not inflated. The proximal portion of the balloon 340 may be fully inflated, in which it radially expands to the full diameter of the balloon 340 without reaching the inside walls of the first cavity 380. Alternatively, the balloon 340 may be partially inflated in which further expansion of the balloon 340 is prevented upon reaching the inside walls of the first cavity 380. Alternatively, the balloon 340 may be partially expanded such that it does not reach its full diameter or come in contact with the inner surface of the mold wall.

Figure 3C:
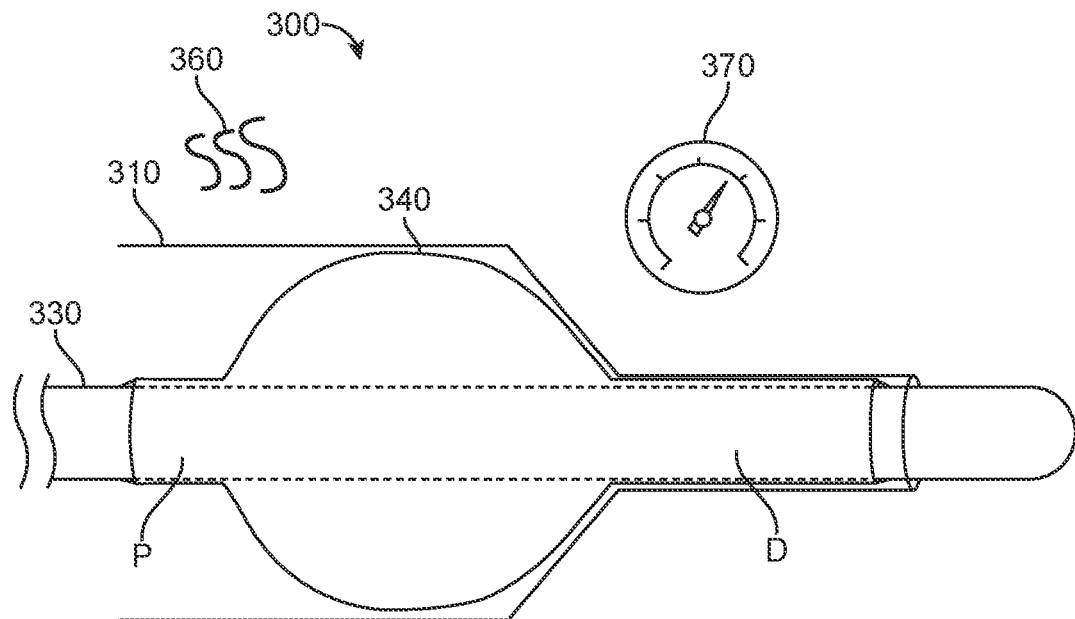
FIG. 3C illustrates a side view of processing a radially expandable member while in a mold.

FIG. 3C shows a side view of processing the balloon while disposed in the mold. In this example the entire balloon 340 may be disposed in the mold and receives treatment, but only the proximal portion of the balloon 340 expands into contact with the larger proximal diameter of the mold and the distal portion of the balloon 340 does not expand as it is constrained by the mold. The treatment may include adding heat 360, pressure 370, or both for a predetermined time. In any example, the added heat 360, pressure 370, or both, may induce shape memory of the balloon 340. Once a stent is placed on the balloon 340, the shape memory may protect the edges of the stent. The shape memory may be a bump or a dumbbell protruding from the edge of the stent that retains its shape after a series of inflating and deflating the balloon 340. Heat 360, pressure 370, or both are applied for a predetermined time, which will induce shape memory to the balloon 340 in the mold. In any example, the heat 360 may be between 40° C. and 80° C., or between 50° C. and 70° C., or between 55° C. and 65° C., or the heat may be 60° C. In any example, the pressure 370 may be between 100 psi and 150 psi, or between 110 psi and 140 psi, or between 110 psi and 130 psi, or between 115 psi and 130 psi, or between 120 psi and 125 psi, or between 120 psi or 125 psi. The dwell time may be the amount of time that heat 360 and pressure 370 is applied. In any example, the dwell time may be between 15 seconds and 2 minutes, or between 15 seconds and 1 minute, or between 30 seconds and 1 minute, or between 1 minute and 1 minute and 30 seconds, or between 1 minute and 30 seconds and 2 minutes, or be 30 seconds, 45 seconds, 1 minute, 1 minute and 15 seconds, 1 minute and 30 seconds, 1 minute and 45 seconds, or 2 minutes. Any combination or permutation of the ranges of time, temperature, or pressure may be used to process the balloon. Although heat 360 and pressure 370 are applied to the entire radially expandable component, only the expanded proximal portion of the balloon 340 will experience shape memory as the distal portion of the balloon 340 is constrained and remains unexpanded. The shape memory will allow the radially expandable portion 340 to keep the protruded pillowed region, even after it has been completely deflated. The proximal portion of the balloon 340 that experiences shape memory will be larger in diameter than the distal portion of the balloon 340 that was constrained. The shape memory added to the proximal portion of the balloon 340 can last more than 2 cycles, 3 cycles, 4 cycles, 5 cycles, 6 cycles, 7 cycles, 8 cycles, 9 cycles, or 10 cycles. A cycle is identified by an inflation of the balloon and a deflation of the balloon during use on a patient.

Figure 3D:
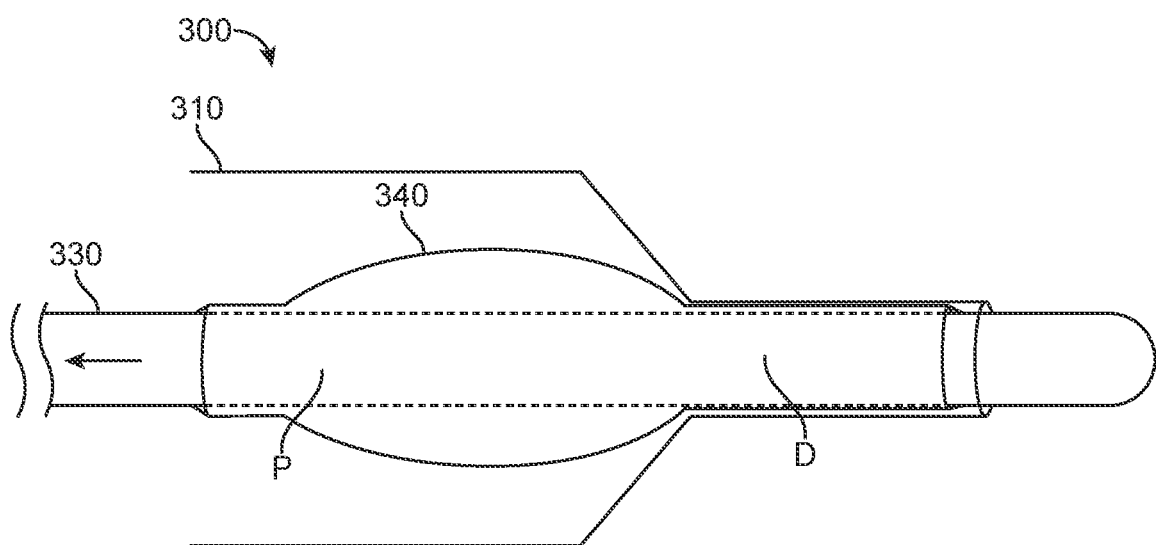
FIG. 3D illustrates a side view of a collapsed radially expandable member in the mold.

FIG. 3D shows a side view of deflating the stent delivery system 300. Here, the balloon 340 is completely deflated, but has a shape memory that creates a bump on the proximal portion of the balloon 340. In another example, the balloon 340 is only partially deflated to retain a larger bump on the edge of the stent (not shown) for insertion into the body. The first catheter 330 coupled to the balloon 340 is then removed from the mold 310 and then a stent may be added to the delivery catheter.

FIG. 4A shows a sideview of a stent delivery system 400 being loaded into a stent 410 after forming the shape memory region or regions in the balloon according to any of the examples disclosed herein. In any example, the stent 410 is loaded onto the balloon 340 in such a way that the proximal end of the stent abuts the pillowed or protruding portion 344 of balloon 340. The "pillowing effect" of the proximal portion of the balloon 340 has a larger diameter than the stent 410. The sheath 335 is pulled over the balloon 340 so that the edge of the sheath passes over the balloon 340 without catching on the stent's edge. The balloon 340 may be collapsed in order to be removed through the sheath 335, or the balloon 340 collapses automatically as it is removed through the sheath 335, however the shape memory remains.

FIG. 4B shows continued proximal retraction 377 of the delivery catheter and stent 410 in FIG. 4A above, into the sheath 335, in which the protruding region 344 of the balloon 340 protects the proximal blunt edge of the stent 410 as it is drawn further proximally, so the stent 410 does not get caught on the sheath 335 when the delivery catheter is being retracted into the sheath 335. The balloon 340 covers the proximal edge of the stent 410 and prevents it from catching on the sheath 335. Additionally, the proximal edge of the stent 410 is protected from dislodgement or damaging tissue during proximal retraction 377 through the vessel.

FIG. 5A shows a side view of loading a proximal portion 520 of the balloon into the mold 510 and the protective sheath 560. FIG. 5A is another example of imparting shape memory to a proximal portion 520 of the balloon similar to FIG. 4B above, with the major difference being the mold 510 and protective sheath 560 used during the processing. In the stent delivery system 500, the mold 510 may be an elongate tube. The mold may be made from metal, polymer, or ceramic, combinations thereof, or any other material known in the art. Alternatively, the mold 510 may be the channel formed by the collapsible iris of a crimping system. Alternatively, the mold 510 may be a plastic tube. In the stent delivery system 500, a first catheter 530 has a distal radiopaque marker 540 and a proximal radiopaque marker 550. The distal radiopaque 540 and proximal radiopaque 550 markers may provide aid in positioning a stent between each radiopaque markers. The proximal portion 520 of the balloon may have a portion that is constrained, and a portion left unconstrained. In this example, the proximal portion of the balloon is left unconstrained. The distal portion of the balloon may be constrained with a protective sheath 560. The protective sheath 560 may be made from metal, plastic, or any other material known in the art. The protective sheath 560 may restrict a portion of the balloon from expanding. Heat and pressure may be applied for a period of time in order to induce expansion of the unconstrained proximal portion 520 of the balloon using any of the processing parameters previously described above. The proximal portion 520 of the balloon may expand until it reaches the wall of the mold 510. The diameter of the mold 510 may determine the diameter of the pillowed portion of the proximal portion 520 of the balloon. The expansion of the proximal portion 520 induces shape memory into the proximal portion 520. The shape memory may be a pillow as described above in the shape of a bump or a dumbbell on the proximal end of the balloon. The shape memory may withstand several cycles (as previously described above) of inflation and deflation of the proximal portion 520. The stent may be loaded onto the balloon such that the proximal edge of the stent abuts the pillow. The shape memory of the proximal portion 520 of the 1 balloon may protect the stent from becoming dislodged or damaged from the retraction of the catheter or causing trauma to tissue as previously described above.

FIG. 5B shows another example that is similar to FIG. 5A, however in this example, a distal portion 525 of the balloon is imparted with a shape memory. In the stent delivery system 500, a protective sheath 560 is loaded onto the proximal portion of the first catheter 530 and over the distal portion 525 of the balloon. Two radiopaque markers may be coupled to the first catheter 530. A proximal radiopaque marker 550 and a distal radiopaque marker 540 are placed on a distal portion of the first catheter 530, the proximal radiopaque marker 550 being proximal to the distal radiopaque marker 540. In any example, the protective sheath 560 may constrain a proximal portion 523 of the distal portion 525 of the balloon and leave a distal portion 527 of the distal portion 525 of the balloon unconstrained. Additionally, a constraining sheath 532 may constrain a further distal portion 529 of the distal portion 525 of the balloon from expansion while a more proximal portion of the distal portion 525 of the balloon is unconstrained and allowed to expand and form a pillow, distal of the distal radiopaque marker 540 where the distal edge of the stent will be. Heat may be applied to the mold 510 and pressure may be applied to the distal portion 525 of the balloon to inflate it, in order to induce shape memory to the distal portion 525 of the balloon as described above. The shape memory may be a bump, or a pillow. The shape memory may withstand several cycles of inflation and deflation of the distal portion 525 of the balloon. The stent may be loaded onto the balloon such that the distal edge of the stent abuts the distal portion 525 of the balloon. The shape memory of the distal portion 525 of the balloon may protect the tissue of the vessel upon delivery.

FIG. 5C shows another example of inducing shape memory. In FIG. 5C, shape memory is induced to both a proximal portion 520 of the balloon as described in FIG. 5A above, and a distal portion 525 of the balloon as described in FIG. 5B above. In any example, the pillowed portion of the distal portion 525 of the balloon may be smaller in diameter than the pillowed portion of the proximal portion 520 of the balloon. This may be due to a lower need for pillowing to protect the surrounding tissue. Alternatively, the pillowed portion of proximal portion 520 of the balloon may have a smaller diameter than the pillowed portion of the distal portion 525 of the balloon. This may be due to a lower concern for tissue damage to the surrounding vasculature upon insertion and retraction, and a larger concern for dislodging of the stent upon insertion and retraction. Alternatively, the pillowed regions of the proximal portion 520 of the balloon and the distal portion 525 of the balloon may have the same size diameter. In this or any example, a protective sheath 560 may be placed between the distal portion 525 of the balloon and proximal portion 520 of the balloon to prevent the middle portion from expanding under heat and pressure. The heat, pressure, and dwell time ranges are discussed above. The sheath 560 may be made from any material discussed above. The first catheter 530 may have two or more radiopaque markers on the distal end of the shaft. The distal radiopaque 540 and proximal radiopaque 550 markers may provide aid in alignment of the protective sheath 560 or the stent. The stent may be disposed between each radiopaque markers. The distal and proximal portions of the balloon 525 and 520, respectively, may expand to come in contact with the mold 510 when heat and pressure are applied.

In another example, as the protective sheath 560 is loaded into the mold 510, placed in between the distal portion 525 of the balloon and proximal portion 520 of the balloon, the proximal portion 520 or the distal portion 525 of the balloon may be fully expanded or partially expanded. When the distal portion 525 and proximal portion 520 of the balloon are partially expanded, they may not come in contact with the mold 510. Alternatively, the distal portion 525 of the balloon may come in contact with the mold when it is fully expanded, while the proximal portion 520 of the balloon does not when it is partially expanded. Or on the contrary, the proximal portion 520 of the balloon may come in contact with the mold 510 when it is fully expanded, while the distal portion 525 of the balloon does not when it is partially expanded. Whether the distal or proximal portions 525 and 520 of the balloon are fully or partially expanded may depend on the desired diameter size of the distal or proximal portions. For example, if a large proximal portion 520 is desired and a smaller distal portion 525 is desired, the proximal portion 520 may be fully expanded and the distal portion 525 may be partially expanded. In any example, the distal and proximal portions 525 and 520 of the balloon may expand at the same time. Alternatively, the proximal portion may expand before the distal portion. Alternatively, the distal portion may expand before the proximal portion.

FIG. 5D shows an example once the balloon has been removed from the mold 510 and the protective sheath 560 has been removed. Shape memory is induced to the proximal portion 520 and the distal portion 525 of the balloon and may survive a series of inflating and deflating the balloon (e.g., balloon) as discussed above. After the shape memory is induced, the stent may be loaded onto the first catheter 530. The stent may be placed between the distal radiopaque 540 and proximal radiopaque 550 markers. A sheath 570 may be inserted onto the balloon.

Figure 5E:
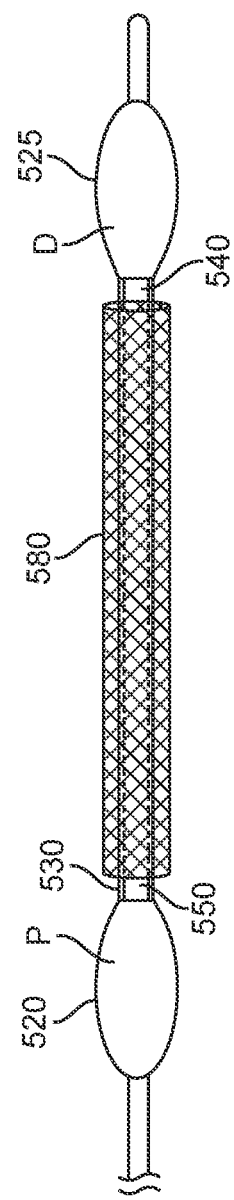
FIG. 5E illustrates a side view of a stent loaded onto a first catheter.

FIG. 5E shows an example once a stent 580 has been loaded onto the first catheter 530 with the pillowed portion of the proximal portion 520 and the distal portion 525 of the balloon. The stent 580 has been placed in between the proximal radiopaque 550 and distal radiopaque 540 markers.

Combined Stent Crimping and Shape Memory Formation

FIG. 6A-6F shows different steps of crimping a stent 610 as it loads over a balloon 620 attached to a distal end of a first catheter 630 for delivery using delivery system 600.

Figure 6A:
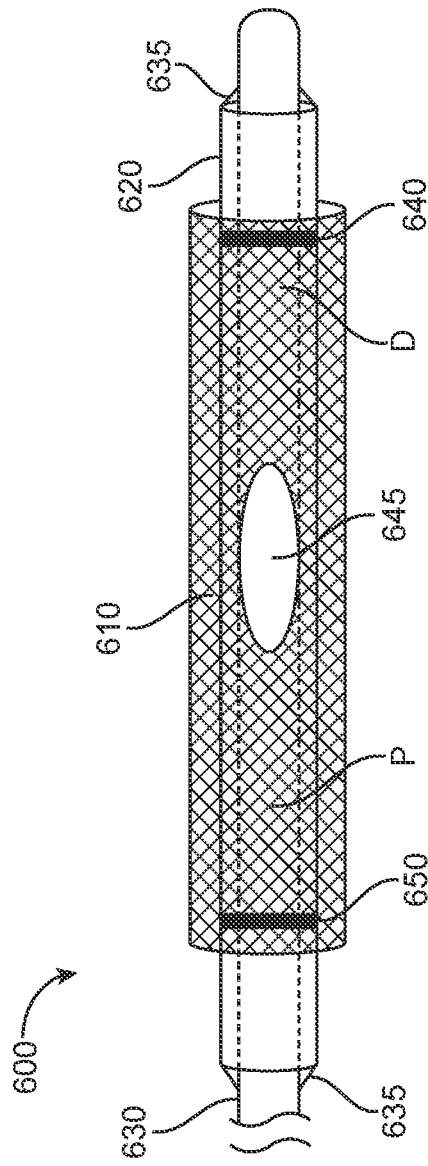
FIG. 6A illustrates a distal portion of another stent delivery system.

FIG. 6A shows a system 600 of crimping the stent 610 and expanding the balloon 620 to form one or more of the pillowed regions previously describe above. In FIG. 6A, the stent 610 is loaded over the balloon 620 that is attached to a distal end of the first catheter 630 for delivery. The working length of the balloon 620 matches the length of the stent 610 while the shoulders 635 may extend slightly beyond the stent. In some examples, the balloon 620 may be longer than the stent 610 and may extend past the stent 610 on either side. The stent 610 may have a side hole 645, or in some examples where a side hole is used, the space between struts on a stent may be used as a side hole. The first catheter 630 may have two or more radiopaque markers that may aid in the stent alignment over the balloon 620. In this example, there are two radiopaque markers; a distal radiopaque marker 640 and a proximal radiopaque marker 650 that is more proximal than the distal radiopaque marker 640. Both of the markers may be on a distal portion of the first catheter.

Figure 6B:
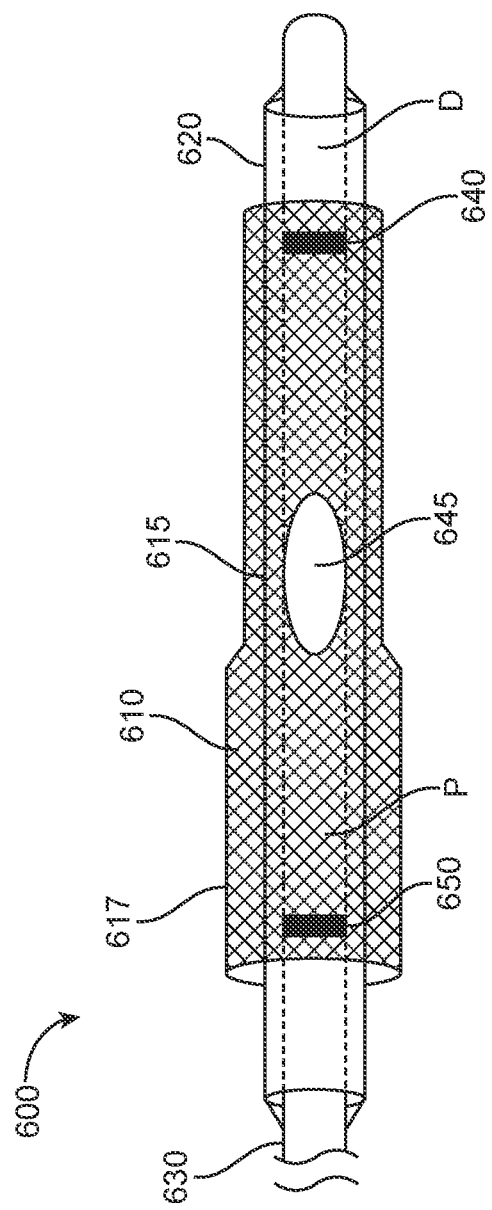
FIG. 6B illustrates the stent of FIG. 6A partially crimped to the delivery system.

In FIG. 6B, a first partial crimp may be applied to a distal portion 615 of the stent 610. The partial crimp provides alignment of the stent onto the balloon 620 and prevents longitudinal movement of the stent 610 so that the stent remains disposed between the radiopaque markers 640, 650. In this or any example, the distal crimp may extend from the distal-most end of the stent up to the side hole 645. In any example, the proximal portion 617 of the stent 610 may not be crimped. The distal crimp of the distal portion 615 may aid in the alignment between the distal radiopaque marker 640 and the proximal radiopaque marker 650 by holding the stent in position. The distal crimp may be made by a light hand crimp or with any other crimping tool. Alternatively, the distal crimp may be made by inserting the system 600 into a crimping iris that applies pressure and heat for a given time. A protective covering may be applied to the proximal portion 617 of the stent 610 in order to prevent expansion. Alternatively, or additionally, the proximal portion 617 is not inserted into the iris to be crimped.

Figure 6C:
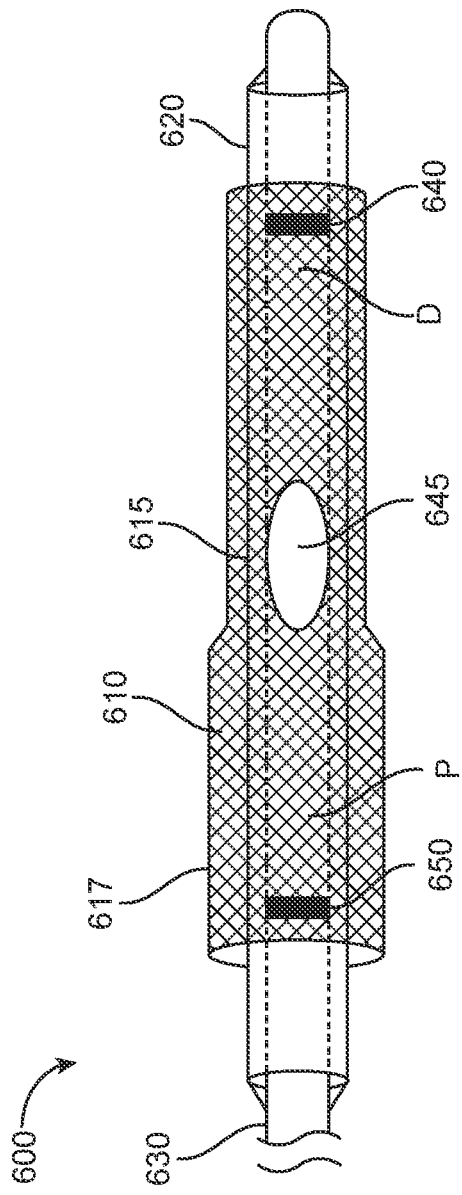
FIG. 6C illustrates the stent of FIG. 6B further crimped to the delivery system.

In FIG. 6C, a full crimp is applied to system 600 that causes the stent 610 to embed into the balloon 620. The full crimp may be applied to the distal portion 615. The full crimp embeds the stent 610 into the balloon 620 and prevents movement or dislodgement of the stent 610. The full crimp may impart some shape memory into the distal portion 615 as heat and pressure is applied for a period of time (refer to operating parameters discussed above), however full expansion may not occur as the dwell time is relatively short in order to crimp the stent. The embedding of the stent into the balloon prevents any longitudinal movement of the stent 610 relative to the balloon 620. Additionally, the full crimp eliminates movement during delivery through a vessel and routine handling and manipulation of the device. A protective covering may be applied to the proximal portion 617 of the stent 610 in order to prevent expansion. Alternatively, or additionally, the proximal portion 617 may not be inserted into the iris to be crimped.

Figure 6D:
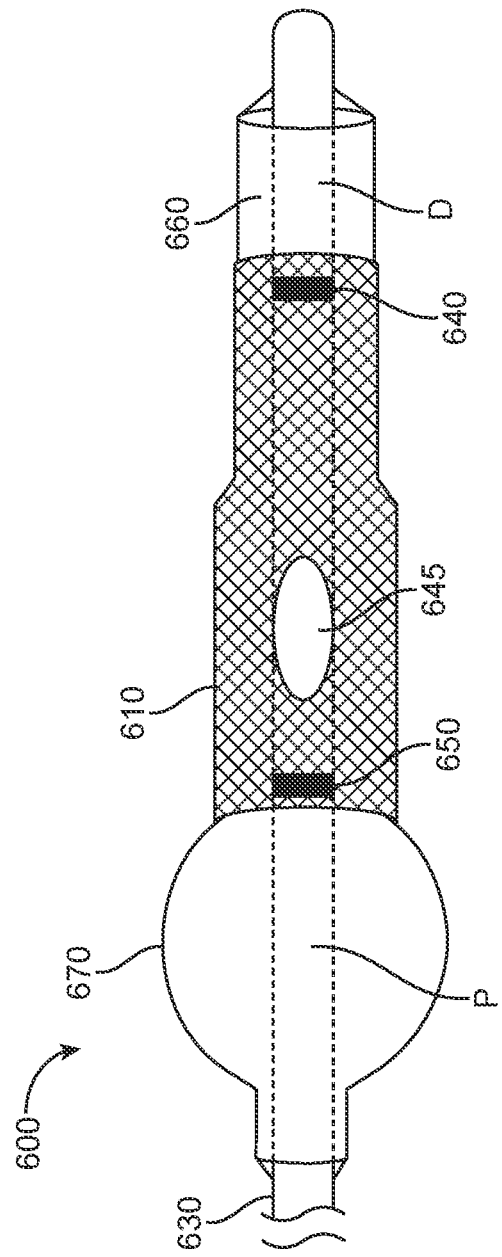
FIG. 6D illustrates pillowing of the radially expandable member in the stent delivery system of FIG. 6C.

FIG. 6D is the system of FIG. 6C, in which the system 600 is inserted into a mold (as described above), heat and pressure are applied for a dwell time to form a shape memory. The mold may be any of the materials or shapes discussed herein. The heat is applied to the mold and pressure is applied to the balloon, in response a portion of the balloon partially inflates to form a dumbbell shape. This may cause a proximal portion 670 of the balloon to expand. Alternatively, this may cause a distal portion 660 of the balloon to expand. In this example, the heat in the mold and pressure in the balloon, causes the proximal 670 and distal portions 660 of the balloon to become pressurized and expand. The proximal portion 670 may be larger in diameter than the distal portion 660. Alternatively, the distal portion 660 may be larger in diameter than a proximal portion 670. Alternatively, the distal portion 660 and the proximal portion 670 may have the same diameter. The heat, pressure, and dwell time that imparts a shape memory may create a bump on the balloon which protrudes to cover the proximal or distal ends, or both ends of the stent 610. Alternatively, the bump may be bulbous or dumbbell in shape. The bump may be maintained even after several cycles of inflating and deflating the balloon.

Figure 6E:
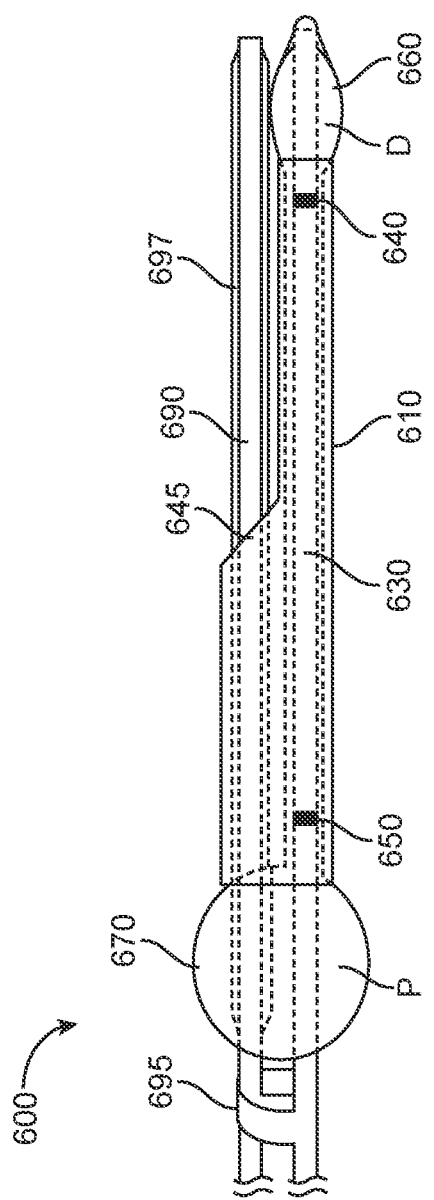
FIG. 6E illustrates the insertion of a second catheter through the stent in FIG. 6D prior to a third crimp of the stent.

FIG. 6E is a 90° rotated side view of FIG. 6D, with the side hole at the top of the stent 610. A second catheter 690 (e.g., daughter catheter or side branch catheter) is inserted into the side hole 645. The second catheter 690 may contain a second balloon 697. In some examples, the second catheter may contain a second stent disposed over the second balloon 697. The first catheter may have a hollow exchange port tube 695 that aids in the alignment of the second catheter 690 with the side hole 645. The hollow exchange port 695 may be made out of glass, plastic, rubber, or any suitable combination thereof. In this example, the second catheter 690 has a distal end that is advanced through the hollow exchange port tube 695 and through the proximal end of the stent 610 before exiting out of an optional side hole 645. The insertion of the second catheter 690 through the side hole 645 of the stent 610 may cause an overlap between the first catheter 630 and the second catheter 690. The second catheter 690 may be introduced through the stent 610 through an existing aperture between adjacent struts in the sidewall of the stent 610.

Figure 6F:
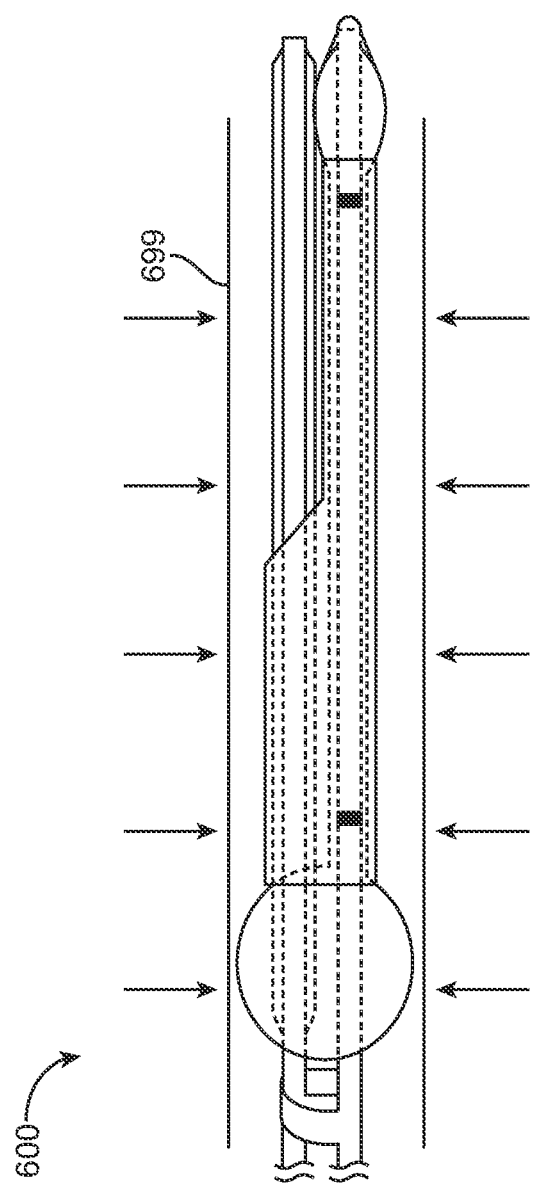
FIG. 6F illustrates the side view of FIG. 6E inserted into a mold for a third crimp.

FIG. 6F shows the system 600 of FIG. 6E inserted into a mold 699. The heat and pressure applied to the system as discussed above crimps the stent to the working length of the balloon on both the first catheter 630 (e.g., mother catheter) and the second catheter 690 (e.g., daughter catheter). The distal region 660 and the proximal region 670 may experience a reduction in diameter as they will be reduced in size, however the dumbbell shape will remain due to the shape memory imparted to these regions of the balloon. The various vertical arrows illustrate the compression force and movement of the mold 699 that will crimp the system 600 together.

NOTES AND EXAMPLES

The following, non-limiting examples, detail certain aspects of the present subject matter to solve the challenges and provide the benefits discussed herein, among others.

Example 1 is a method for retaining a stent, comprising: providing a stent delivery system comprising a first elongate shaft and a first radially expandable member disposed on a distal portion of the first elongate shaft, wherein the first elongate shaft further comprises a distal radiopaque marker on a distal portion of the first elongate shaft and a proximal radiopaque marker disposed on a distal portion of the first elongate shaft, the proximal marker proximal of the distal marker; inserting the first radially expandable member into a cavity in a mold; partially crimping a distal portion of the stent onto the first radially expandable member to hold the stent in alignment between the proximal and distal radiopaque markers; fully crimping the distal portion of the stent onto the first radially expandable member, wherein fully crimping embeds the stent onto the first radially expandable member; and applying heat and pressure to the first radially expandable member while disposed in the cavity in the mold, thereby imparting a shape memory to a portion of the first radially expandable member.

Example 2 is the method of Example 1, wherein the first radially expandable member is a balloon; and wherein imparting the shape memory further comprises constraining the portion of the first radially expandable member by the mold, while other parts of the first radially expandable member are unconstrained by the mold.

Example 3 is the method of any of Examples 1-2, wherein the first radially expandable member comprises a proximal portion, a distal portion, and an intermediate portion disposed therebetween, wherein the imparting the shape memory further comprises imparting the shape memory to the proximal portion without imparting the shape memory to the distal portion or the intermediate portion, or wherein the imparting the shape memory further comprises imparting the shape memory to the distal portion without imparting the shape memory to the proximal portion or the intermediate portion, or wherein the imparting the shape memory further comprises imparting the shape memory to the distal portion and the proximal portion without imparting the shape memory to the intermediate portion.

Example 4 is the method of any of Examples 1-3, wherein imparting the shape memory to the proximal portion without imparting the shape memory to the distal portion or the intermediate portion further comprises forming the proximal portion of the first radially expandable member so that the proximal portion has a diameter larger than a diameter of the distal portion of the first radially expandable member, or wherein the imparting the shape memory to the distal portion and the proximal portion without imparting the shape memory to the intermediate portion further comprises forming the proximal portion of the first radially expandable member so that the proximal portion may have a diameter smaller than a diameter of the distal portion of the first radially expandable member.

Example 5 is the method of any of Examples 1-4, wherein crimping the distal portion of the stent comprises partially crimping the distal portion, wherein crimping the distal portion of the stent further comprises a second crimping after the partially crimping, and wherein the second crimping further comprises fully crimping the distal portion of the stent to the first radially expandable member without crimping the proximal portion onto the first radially expandable member.

Example 6 is the method of any of Examples 1-5, wherein crimping the distal portion of the stent further comprises fully crimping the distal portion of the stent to the first radially expandable member, wherein crimping the distal portion of the stent further comprises a second full crimping after fully crimping, and wherein the second full crimping further comprises fully crimping the distal and proximal portions of the stent to the first radially expandable member.

Example 7 is the method of any of Examples 1-6, wherein the shape memory is maintained after a plurality of cycles of inflating and deflating the radially expandable member, and wherein the shape memory comprises a bulbous region, wherein the bulbous region is configured to abut an edge of the stent and provide a protective cover to the edge of the stent.

Example 8 is the method of any of Examples 1-7, wherein the bulbous region is configured to have a diameter larger than a diameter of the edge of the stent.

Example 9 is the method of any of Examples 1-8, further comprising: slidably disposing a second elongate shaft having a second radially expandable member under the proximal portion of the first stent and through a side hole of the stent after fully crimping; and simultaneously crimping the stent onto the first radially expandable member and the second radially expandable member.

Example 10 is the method of any Examples 1-9, wherein the first elongate shaft further comprises a hollow exchange port tube coupled to an outer surface of the first elongate shaft, the hollow exchange port tube having a lumen disposed therethrough, and wherein inserting the second radially expandable member further comprises: slidably disposing the second elongate shaft through the lumen of the hollow exchange port tube such that the second elongate shaft is aligned with the side hole of the stent.

Example 11 is the method of any Examples 1-10, wherein the shape memory is maintained after a plurality of cycles of inflating and deflating the first radially expandable member, and wherein the shape memory comprises a bulbous region, wherein the bulbous region is configured to abut an edge of the stent and provide a protective cover to the edge of the stent.

Example 12 is a system for retaining a stent, comprising: a stent delivery system comprising a first elongate shaft and a first radially expandable member disposed on a distal portion of the first elongate shaft, the first elongate shaft further comprising a distal radiopaque marker on a distal portion of the first elongate shaft and a proximal radiopaque marker disposed on a distal portion of the first elongate shaft, the proximal marker proximal of the distal marker; a mold comprising a cavity, wherein the first radially expandable member is disposed in the cavity and a stent disposed onto the first radially expandable member such that the stent is disposed between the distal radiopaque marker and the proximal radiopaque marker, wherein the stent comprises a proximal portion and a distal portion, and wherein the distal portion of the stent is fully crimped to the first radially expandable member and the proximal portion is uncrimped to the first radially expandable member, such that full crimp prevents axial movement of the stent during delivery; and a region of the first radially expandable member comprising a shape memory portion comprising a first bulbous region abutting an edge of the stent to provide a protective cover to the edge of the stent.

Example 13 is the system of Example 12, wherein the first radially expandable member is a balloon.

Example 14 is the system of any of Examples 12-13, wherein the first radially expandable member further comprises a proximal portion, a distal portion, and an intermediate portion disposed therebetween, wherein the shape memory portion is imparted to the proximal portion without the shape memory portion being imparted to the distal portion or the intermediate portion, or wherein the shape memory portion is imparted to the distal portion without the shape memory portion being imparted to the proximal portion or the intermediate portion, or wherein the shape memory portion is imparted to the distal portion and the proximal portion without the shape memory portion being imparted to the intermediate portion.

Example 15 is the system of any of Examples 12-14, wherein when the shape memory portion is imparted to the proximal portion without the shape memory being imparted to the distal portion or the intermediate portion, or wherein the shape memory is imparted to the distal portion and the proximal portion without the shape memory being imparted to the intermediate portion, the proximal portion of the first radially expandable member has a diameter larger than a diameter of the distal portion of the first radially expandable member.

Example 16 is the system of any of Examples 12-15, wherein the distal and proximal portions of the stent are fully crimped to the first radially expandable member.

Example 17 is the system of any of Examples 12-16, wherein the shape memory portion is maintained after a plurality of cycles of inflation and deflation of the first radially expandable member Example 18 is the system of any of Examples 12-17, wherein the stent comprises a side wall with a side hole extending therethrough, and wherein the first elongate shaft further comprises a hollow exchange port tube coupled to an outer surface of the first elongate shaft, the hollow exchange port tube having a lumen disposed therethrough and wherein a second elongate shaft is slidably disposed through the lumen of the hollow exchange port tube such that the second elongate shaft is aligned with the side hole of the stent.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method for retaining a stent, comprising:
providing a stent delivery system comprising a first elongate shaft and a first radially expandable member disposed on a distal portion of the first elongate shaft, wherein the first elongate shaft further comprises a distal radiopaque marker on a distal portion of the first elongate shaft and a proximal radiopaque marker disposed on the distal portion of the first elongate shaft, the proximal marker proximal of the distal marker;
inserting the first radially expandable member into a cavity in a mold;
partially crimping a distal portion of the stent onto the first radially expandable member to hold the stent in alignment between the proximal and distal radiopaque markers;
fully crimping the distal portion of the stent onto the first radially expandable member, wherein fully crimping embeds the stent onto the first radially expandable member;
applying heat and pressure to the first radially expandable member while disposed in the cavity in the mold, thereby imparting a shape memory to a portion of the first radially expandable member; and slidably disposing a second elongate shaft having a second radially expandable member under a proximal portion of the stent and through a side hole of the stent after the fully crimping; and simultaneously crimping the stent onto the first radially expandable member and the second radially expandable member.

2. The method of claim 1, wherein the first radially expandable member is a balloon, and wherein imparting the shape memory further comprises constraining the portion of the first radially expandable member by the mold, while other parts of the first radially expandable member are unconstrained by the mold.

3. The method of claim 1, wherein the first radially expandable member comprises a proximal portion, a distal portion, and an intermediate portion disposed therebetween, wherein the imparting the shape memory further comprises imparting the shape memory to the proximal portion of the first radially expandable member without imparting the shape memory to the distal portion of the first radially expandable member or the intermediate portion of the first radially expandable member, or wherein the imparting the shape memory further comprises imparting the shape memory to the distal portion of the first radially expandable member without imparting the shape memory to the proximal portion of the first radially expandable member or the intermediate portion of the first radially expandable member, or wherein the imparting the shape memory further comprises imparting the shape memory to the distal portion of the first radially expandable member and the proximal portion of the first radially expandable member without imparting the shape memory to the intermediate portion of the first radially expandable member.

4. The method of claim 3, wherein imparting the shape memory to the proximal portion of the first radially expandable member without imparting the shape memory to the distal portion of the first radially expandable member or the intermediate portion of the first radially expandable member further comprises forming the proximal portion of the first radially expandable member so that the proximal portion of the first radially expandable member has a diameter larger than a diameter of the distal portion of the first radially expandable member, or wherein the imparting the shape memory to the distal portion of the first radially expandable member and the proximal portion of the first radially expandable member without imparting the shape memory to the intermediate portion of the first radially expandable member further comprises forming the proximal portion of the first radially expandable member so that the proximal portion of the first radially expandable member has a diameter smaller than a diameter of the distal portion of the first radially expandable member.

5. The method of claim 1, wherein the shape memory is maintained after a plurality of cycles of inflating and deflating the radially expandable member, and wherein the shape memory comprises a bulbous region, wherein the bulbous region is configured to abut an edge of the stent and provide a protective cover to the edge of the stent.

6. The method of claim 5, wherein the bulbous region is configured to have a diameter larger than a diameter of the edge of the stent.

7. The method of claim 1, wherein the first elongate shaft further comprises a hollow exchange port tube coupled to an outer surface of the first elongate shaft, the hollow exchange port tube having a lumen disposed therethrough, and wherein inserting the second radially expandable member further comprises slidably disposing the second elongate shaft through the lumen of the hollow exchange port tube such that the second elongate shaft is aligned with the side hole of the stent.

8. The method of claim 1, wherein the shape memory is maintained after a plurality of cycles of inflating and deflating the first radially expandable member, and wherein the shape memory comprises a bulbous region, wherein the bulbous region is configured to abut an edge of the stent and provide a protective cover to the edge of the stent.

* * * * *

UNITED STATES PATENT AND TRADEMARK OFFICE
CERTIFICATE OF CORRECTION

PATENT NO. : 12,274,633 B2
APPLICATION NO. : 17/885723
DATED : April 15, 2025
INVENTOR(S) : Bourang et al.

Page 1 of 1

It is certified that error appears in the above-identified patent and that said Letters Patent is hereby corrected as shown below:

In the Specification

In Column 7, Line 62, delete "1 balloon" and insert --balloon-- therefor

In Column 13, Line 45, after "member", insert --.--

Signed and Sealed this
Third Day of June, 2025

Coke Morgan Stewart
*Acting Director of the United States Patent and Trademark Office*